United States Patent [19]

Harada et al.

[11] Patent Number: 4,839,333
[45] Date of Patent: Jun. 13, 1989

[54] RECORDING MATERIAL CONTAINING LEUCO DYE

[75] Inventors: Toru Harada; Naoki Saito; Kozo Sato, all of Kanagawa, Japan

[73] Assignee: Fuji Photo Film Co., Ltd., Kanagawa, Japan

[21] Appl. No.: 178,935

[22] Filed: Apr. 7, 1988

[30] Foreign Application Priority Data

Apr. 7, 1987 [JP] Japan .................. 62-85533

[51] Int. Cl.$^4$ .................. B41M 5/16; B41M 5/18; B41M 5/22
[52] U.S. Cl. .................. 503/218; 427/151; 428/341; 428/342; 428/913; 428/914
[58] Field of Search .................. 427/150–152; 428/341, 342, 913, 914; 503/217, 218, 223

[56] References Cited

U.S. PATENT DOCUMENTS 3,967,835 7/1976 Ozutsumi et al. .................. 503/218

FOREIGN PATENT DOCUMENTS 0179378 4/1986 European Pat. Off. ............ 503/218

Primary Examiner—Bruce H. Hess
Attorney, Agent, or Firm—Sughrue, Mion, Zinn, Macpeak & Seas

[57] ABSTRACT

A recording material comprises a layer containing a leuco dye provided on a support, characterized in that the leuco dye has the following formula (I):

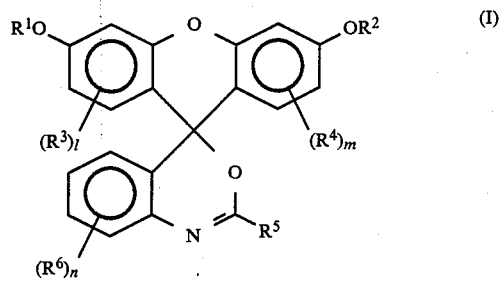

in which each of $R^1$ and $R^2$ independently is an alkyl group, a cycloalkyl group or an aralkyl group; each of $R^3$ and $R^4$ independently is a halogen atom, an alkyl group, a cycloalkyl group, an aralkyl group, alkoxy group or an acylamino group; $R^5$ is an alkyl group, a cycloalkyl group, an aralkyl group, an alkoxy group, an aryloxy group, a dialkylamino group, an alkoxycarbonyl group, an aryloxycarbony group, a dialkylcarbamoyl group, an aryl group or a heterocyclic group; $R^6$ is a halogen atom, an alkyl group, an alkoxy group, hydroxyl, amino, an alkylamino group, a dialkylamino group, an acylamino group, nitro, cyano, carbamoyl, sulfamoyl, an aryloxycarbonyl group, an alkoxycarbonyl group, an alkylsulfonyl group, an arylsulfonyl group, an alkylsufonylamino group, an arylsulfonylamino group or an aryl group; l is 0 or 1; m is 0 or 1; n is 0, 1, 2, 3 or 4; and each of $R^1$, $R^2$, $R^3$, $R^4$, $R^5$ and $R^6$ may have one or more substituent groups.

12 Claims, No Drawings

RECORDING MATERIAL CONTAINING LEUCO DYE

FIELD OF THE INVENTION

This invention relates to a recording material such as a pressure-sensitive material, a heat-sensitive material and a light-sensitive material, and more particularly to a recording material containing a leuco dye.

BACKGROUND OF THE INVENTION

In various recording materials including pressure-sensitive, heat-sensitive and light-sensitive materials, a leuco dye is frequently used as a color image forming substance. The leuco dye, which is also referred to as a redox dye, develops a color on contact with an acid color developer.

The leuco dye is generally contained in microcapsules which are dispersed in a recording material. In an image forming process, the microcapsules are broken by external energy such as pressure and/or heat so that the dye comes into contact with the acid color developer which has been arranged outside of the microcapsules in the recording material.

Examples of the leuco dye which develops a yellowish color are described in Japanese Patent Publication Nos. 45(1970)-4698, 50(1975)-24646, 51(1976)-27169 and 53(1978)-9127 (corresponding British Pat. No. 1421493), and Japanese Patent Provisional Publication No. 49(1969)-4480. However, these leuco dyes do not satisfy the requirement with respect to light fastness, that is, the developed color tends to fade from the image when it is irradiated with light.

SUMMARY OF THE INVENTION

An object of the present invention is to provide a recording material which gives a yellow color image improved in the color density and the light fastness.

There is provided by the present invention a recording material comprising a layer containing a leuco dye provided on a support, wherein the leuco dye is a novel leuco dye having the following formula (I):

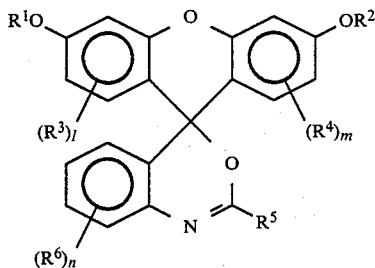

in which each of $R^1$ and $R^2$ independently is a monovalent group selected from the group consisting of an alkyl group, a cycloalkyl group and an aralkyl group; each of $R^3$ and $R^4$ independently is a monovalent group selected from the group consisting of a halogen atom, an alkyl group, a cycloalkyl group, an aralkyl group, an alkoxy group and an acylamino group; $R^5$ is a monovalent group selected from the group consisting of an alkyl group, a cycloalkyl group, an arlalkyl group, an alkoxy group, an arloxy group, a dialkylamino group, an alkoxycarbonyl group, an aryloxycarbonyl group, a dialkylcarbamoyl group, an aryl group and a heterocyclic group; $R^6$ is a monovalent group selected from the group consisting of a halogen atom, an alkyl group, an alkoxy group, hydroxyl, amino, an alkylamino group, a dialkylamino group, an acylamino group, nitro, cyano, carbamoyl, sulfamoyl, an aryloxycarbonyl group, an alkoxycarbonyl group, an alkylsulfonyl group, an arylsulfonyl group, an alkylsulfonylamino group, an arylsulfonylamino group and an aryl group; l is 0 or 1; m is 0 or 1; n is 0, 1, 2, 3 or 4 (when n is 2, 3 or 4, the groups represented by $R^6$ may be different from each other); each of $R^1$, $R^2$, $R^3$, $R^4$, $R^5$ and $R^6$ may have one or more substituent groups.

The present inventors have found that the novel leuco dye having the formula (I) is improved in not only the color developing rate but also the density and the light fastness of the developed color. Therefore, the leuco dye can be advantageously used as a color image forming substance (yellow color image forming substance) for a recording material.

The developed yellow color of the leuco dye is especially suitable for a monochromatic recording material. Therefore, the recording material of the invention is preferably used as a pressure-sensitive material or a heat-sensitive material.

DETAILED DESCRIPTION OF THE INVENTION

The leuco dye employed in the present invention has the following formula (I):

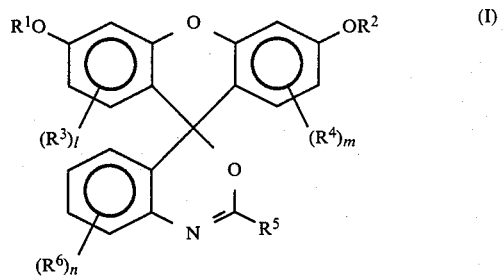

In the formula (I), each of $R^1$ and $R^2$ independently is an alkyl group, a cycloalkyl group or an aralkyl group. Among them, an alkyl group and an aralkyl group are preferred. Further, an alkyl group is more preferred.

Each of $R^3$ and $R^4$ independently is a halogen atom, an alkyl group, a cycloalkyl group, an aralkyl group, alkoxy group or an acylamino group. Among them, a halogen atom, an alkyl group and a cycloalkyl group are preferred. Further, each of "l" and "m" independently is 0 or 1.

$R^5$ is an alkyl group, a cycloalkyl group, an aralkyl group, an alkoxy group, an aryloxy group, a dialkylamino group, an alkoxycarbonyl group, an aryl group, an aryloxycarbonyl group, a dialkylcarbamoyl group, an aryl group or a heterocyclic group. Among them an alkyl group, a cycloalkyl group, an alkoxy group, an alkoxycarbonyl group, an aryl group and a heterocyclic group are preferred. Further, an alkyl group, an aryl group and a heterocyclic group are more preferred.

$R^6$ is a halogen atom, an alkyl group, an alkoxy group, hydroxyl, amino, an alkylamino group, a dialkylamino group, an acylamino group, nitro, cyano, carbamoyl, sulfamoyl, an aryloxycarbonyl group, an alkoxycarbonyl group, an alkylsulfonyl group, an arylsulfonyl group, an alkylsulfonylamino group, an arylsulfonylamino group or an aryl group. Among them, a halogen atom, an acylamino group and an alkylsulfonyl group are preferred. Further, "n" is 0, 1, 2, 3 or 4. When "n" is 2, 3 or 4, the groups represented by $R^6$ may be different from each other. However, "n" preferably is 0.

Each of $R^1$, $R^2$, $R^3$, $R^4$, $R^5$ and $R^6$ may have one or more substituent groups.

The alkyl group represented by $R^1$, $R^2$, $R^3$, $R^4$, $R^5$ and $R^6$ preferably has 1 to 22 carbon atoms, more preferably has 1 to 12 carbon atoms. The alkyl group may be of a straight chain or a branched chain, and may have one or more substituent groups such as a halogen atom, cyano, an alkoxy group or hydroxyl.

Examples of the cycloalkyl group represented by $R^1$, $R^2$, $R^3$, $R^4$ and $R^5$ include cyclopentyl, cyclohexyl, cycloheptyl and cyclooctyl.

Examples of the aralkyl group represented by $R^1$, $R^2$, $R^3$, $R^4$ and $R^5$ include benzyl and phenytyl. The aryl moiety of the aralkyl group may have one or more substituent groups such as a halogen atom, a lower alkyl group (having 1 to 4 carbon atoms), a lower alkoxy group (having 1 to 4 carbon atoms), and nitro.

The halogen atom represented by $R^3$, $R^4$ and $R^6$ preferably is chlorine or bromine.

Examples of the aryl group represented by $R^5$ and $R^6$ include phenyl and naphtyl. The aryl group may have one or more substituent groups such as a halogen atom, a lower alkyl group (having 1 to 4 carbon atoms), a lower alkoxy group (having 1 to 4 carbon atoms) and nitro.

The alkyl moiety of the alkoxy group represented by $R^3$, $R^4$, $R^5$ and $R^6$ preferably has 1 to 12 carbon atoms. The alkyl moiety may have one or more substituent groups such as cyano, a halogen atom, an alkoxy group and hydroxyl.

The acylamino group represented by $R^3$, $R^4$ and $R^6$ has the formula represented by $-NR^8COR^7$, wherein $R^7$ is a monovalent group selected from the group consisting of an alkyl group and an aryl group; $R^8$ is a monovalent group selected from the group consisting of hydrogen, an alkyl group and an aryl group. The alkyl group represented by $R^8$ preferably has 1 to 22 carbon atoms, more preferably has 1 to 12 carbon atoms. The alkyl group may be of a straight chain or a branched chain and may have one or more substituent groups such as a halogen atom, cyano, an alkoxy group and hydroxyl. Examples of the aryl group include phenyl and naphtyl. The aryl group may have one or more substituent groups such as a halogen atom, a lower alkyl group (having 1 to 4 carbon atoms), a lower alkoxy group (having 1 to 4 carbon atoms) and nitro.

Examples of the aryl moieties of the aryloxycarbonyl group represented by $R^5$ and $R^6$, the aryloxy group represented by $R^5$, the arylsulfonyl group represented by $R^6$ and the arylsulfonylamino group represented by $R^6$ include phenyl and naphtyl. The aryl moieties may have one or more substituent groups such as a halogen atom, a lower alkyl group (having 1 to 4 carbon atoms), a lower alkoxy group (having 1 to 4 carbon atoms) and nitro.

The alkyl moieties of the dialkylamino group represented by $R^5$ and $R^6$, the dialkylcarbomoyl group represented by $R^5$, the alkylamino group represented by $R^6$, the alkylsulfonyl group represented by $R^6$ and the alkylsulfonylamino group represented by $R^6$ preferably have 1 to 22 carbon atoms, and more preferably have 1 to 12 carbon atoms. The alkyl moieties may be of a straight chain or a branched chain, and may have one or more substituent groups such as a halogen atom, cyano, an alkoxy group, hydroxyl.

The alkyl moiety of the alkoxycarbonyl group represented by $R^5$ and $R^6$ preferably has 1 to 12 carbon atoms. The alkyl moiety may have one or more substituent groups such as cyano, a halogen atom, an alkoxy group and hydroxyl.

Examples of the hetero atoms of the heterocyclic group represented by $R^5$ include nitrogen, oxygen and sulfur. The heterocyclic group may be of a monocyclic ring or a condensed hetrocyclic ring.

The carbamoyl group represented by $R^6$ has the formula represented by $-CONR^9R^{10}$, wherein each of $R^9$ and $R^{10}$ independently is hydrogen, an alkyl group or an aryl group.

The sulfamoyl group represented by $R^6$ has the formula represented by $-SO_2NR^{11}R^{12}$, wherein each of $R^{11}$ and $R^{12}$ is hydrogen, an alkyl group or an aryl group.

Examples of the leuco dyes which are preferably used in the invention are described hereinafter.

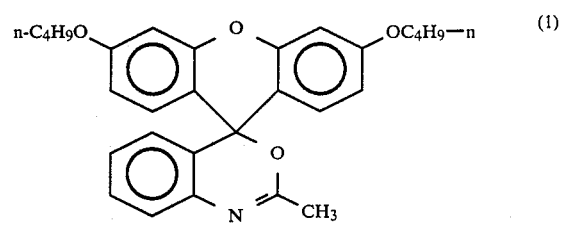

(1)

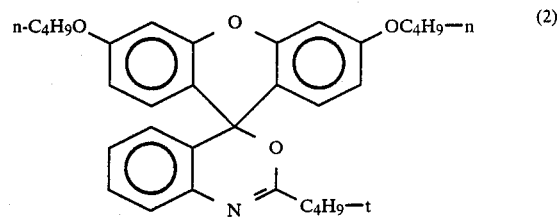

(2)

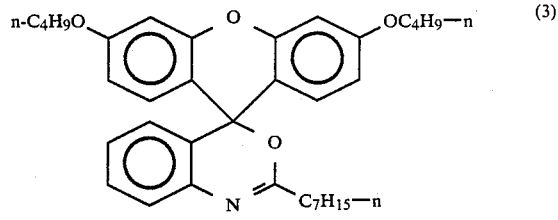

(3)

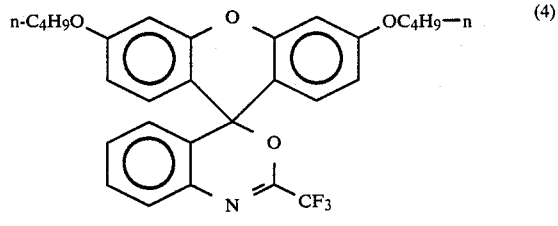

(4)

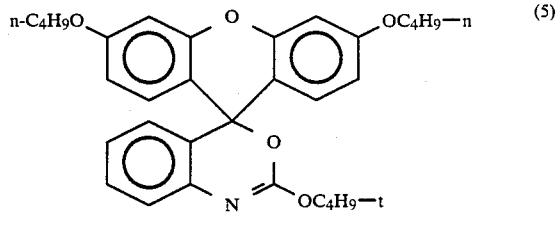

(5)

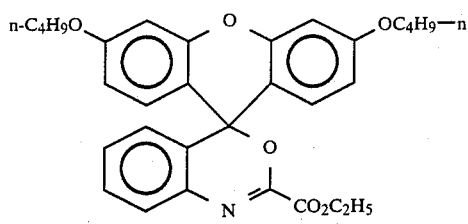
(6)
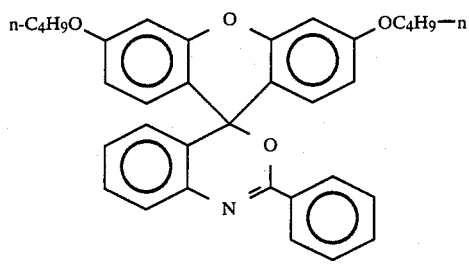
(7)
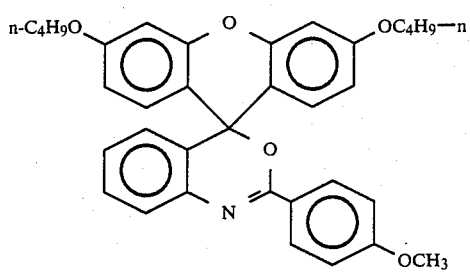
(8)
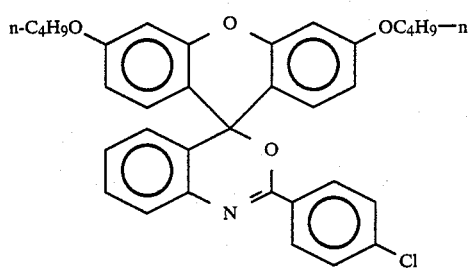
(9)
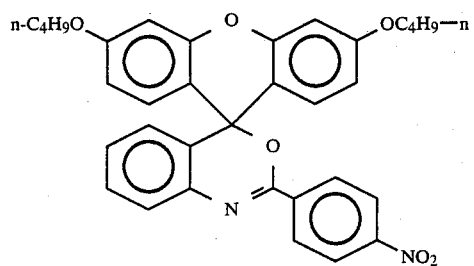
(10)
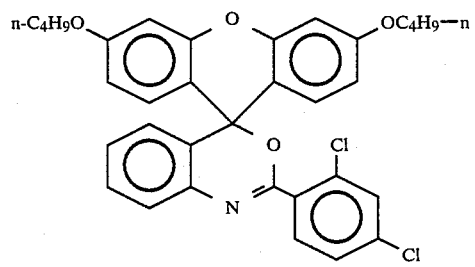
(11)
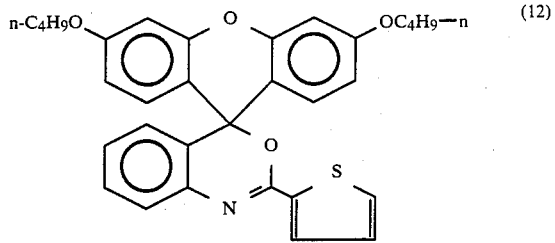
(12)
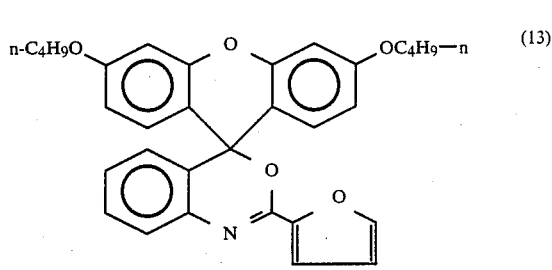
(13)
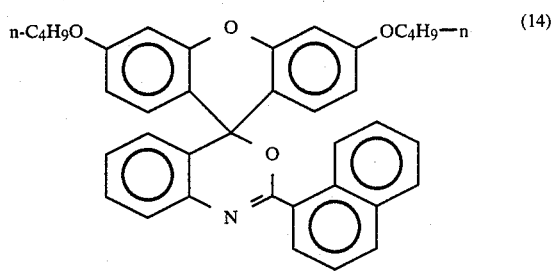
(14)
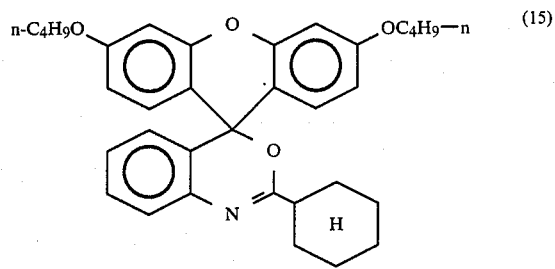
(15)
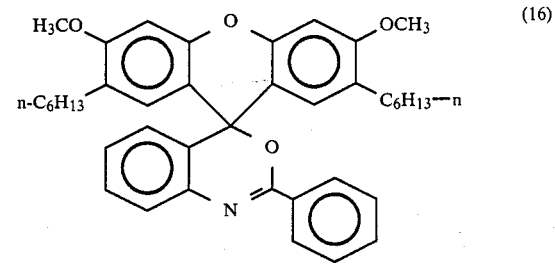
(16)
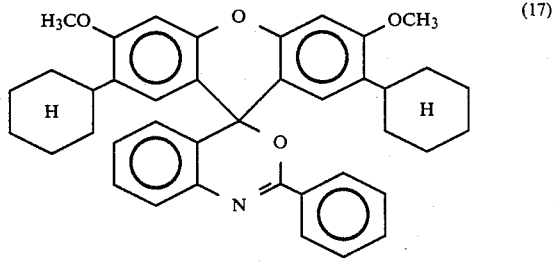
(17)

-continued
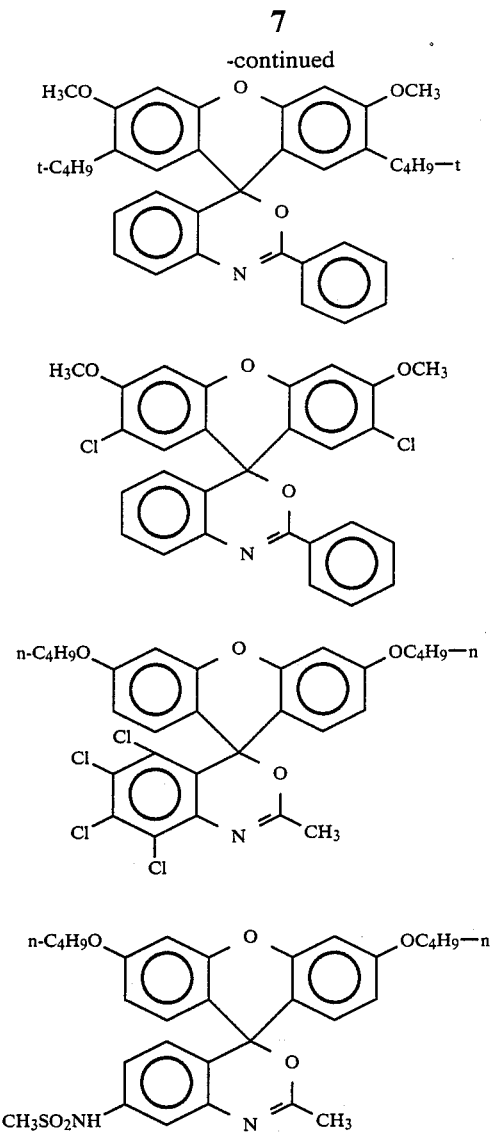
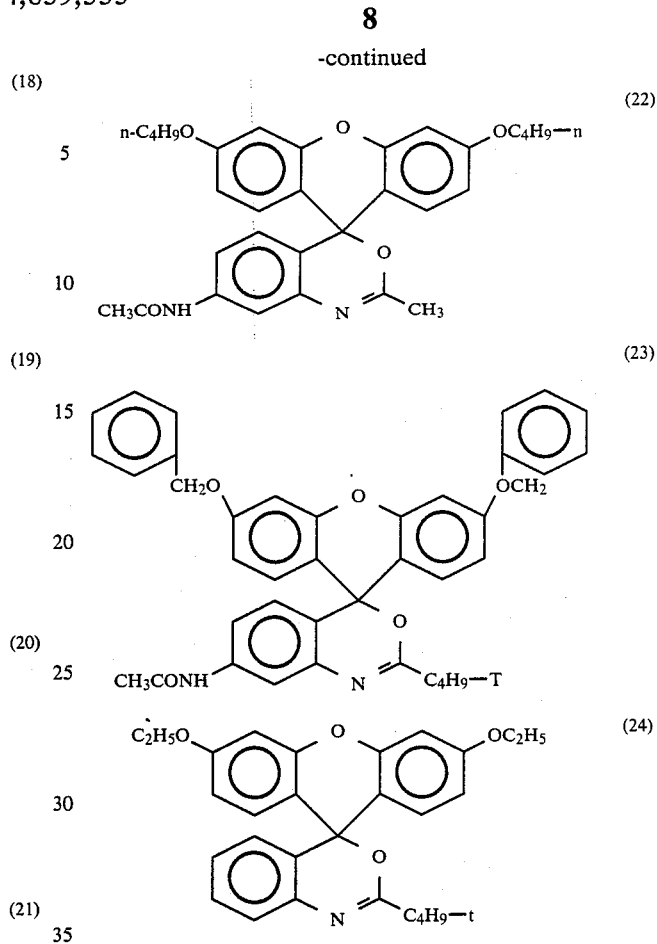
The leuco dyes used in the present invention can be easily synthesized by the following procedure.
SYNTHESIS EXAMPLE 1
Synthesis of leuco dye (1)
The leuco dye (1) was synthesized by way of the compounds of the following formulas (i) to (v):
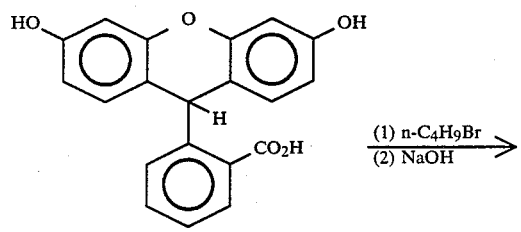
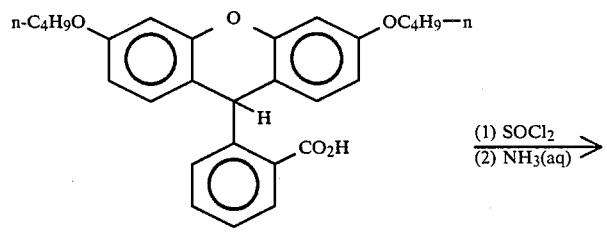
(i)

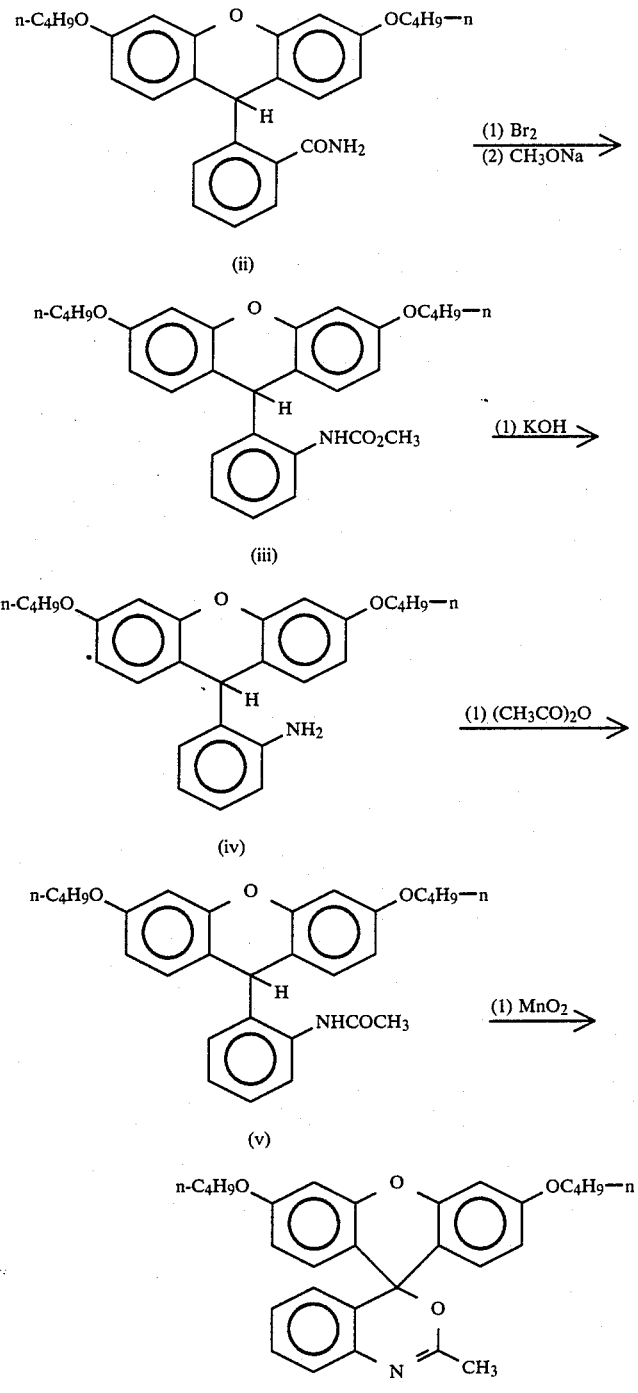

Leuco Dye (1)

Synthesis of compound (i)

In a three-necked flask were placed 221 g of fluoresceine, 453 g of n-butylbromide, 455 g of potassium carbonate and 500 ml of N,N-dimethylacetoamide, and the mixture was reacted at 90° C. for 4 hours. The reaction mixture was then poured into 3 l of water, and extracted with 500 ml of ethyl acetate. The extract was then concentrated under reduced pressure.

To the obtained oil were added 700 ml of ethyl alcohol and 160 ml of an aqueous solution containing 80 g of sodium hydroxyde, and the mixture was heated while stirring for 30 minutes. The reaction mixture was added to a mixture of 2 l of water and 160 ml of hydrochloric acid to obtain a crystalline precipitate. The precipitate was filtered. The filtrate was washed with acetonitrile, and then dried to obtain a compound of the formula (i). The yield was 245 g, m.p. 156°–157° C.

Synthesis of compound (ii)

To 600 ml of benzene were added 245 g of the compound (i) obtained above and 48 ml of thionyl chloride, and the mixture was refluxed for 2 hours. The reaction mixture was concentrated under reduced pressure, and to the mixture was added 500 ml of acetonitrile. To the resulting mixture was dropwise added 250 ml of an aqueous ammonia while cooling the mixture by means of ice. The mixture was then stirred for 1 hour at room temperature. To the mixture was poured 500 ml of ice-cooled water and then added 250 ml of hydrochloric acid to obtain a crystalline precipite. The precipitate was then collected by filtration. The filtrate was washed with acetonitrile, and then dried to obtain a compound of the formula (ii). The yield was 220 g, m.p. 152°–153° C.

Synthesis of compound (iii)

In a mixture of 1 l of toluene and 1 l of methyl alcohol was dissolved 178 g of the compound (ii) obtained above, and to the resulting mixture was added 160 ml of 28% methyl alcohol solution of sodium methylate at a temperature of not higher than 20° C. To the mixture was further added 20.5 ml of potassium bromide at a temperature of not higher than 15° C. The resulting mixture was stirred for 30 minutes at room temperature, and was then concentrated under reduced pressure and purified by column chromatography (solvent; ethyl acetate/n-hexan=6/1) to obtain a compound of the formula (iii). The yield was 132 g, m.p. 90°–92° C.

Synthesis of compound (iv)

In a flask were placed 130 g of the compound (iii) obtained above, 2.0 l of methylcellosorb and 200 ml of an aqueous solution containing 125 g of potassium hydroxyde, and the mixture was stirred for 2 hours under the external condition at 120° C. The resulting mixture was concentrated under reduced pressure. To the concentration were added 1 l of water and 700 ml of ethyl acetate in order and the mixture was extracted. The extract was concentrated under reduced pressure, and to the concentrate was added 700 ml of methyl acetate. The mixture was stirred at room temperature for 2 hours to obtain a crystalline precipitate. The precipitate was filtered to obtain a compound of the formula (iii). The yield was 80 g, m.p. 90°–92° C.

Synthesis of compound (v)

In a flask was placed 5 g of the compound (iv) obtained above, 5 ml of acetic anhydride and 40 ml of benzene, and the mixture was heated while stirring for 1 hour. The reaction mixture was concentrated under reduced pressure, and into the mixture was poured water. The mixture was filtered to obtain crystalline precipitate. The precipitate was washed with acetonitrile and dried to obtain a compound of the formula (v). The yield was 5 g, m.p. 169°–170° C.

Synthesis of leuco dye (1)

In a flask were placed 5 g of the compound (v) obtained above, 20 ml of ethyl acetate and 15 g of manganese dioxide, and the mixture was heated while stirring for 1 hour. The reaction mixture was filtered, and the filtrate was concentrated. The concentration was then purified by column chromatography (solvent; n-hexane/ethyl acetate=5/1) to obtain a leuco dye (1). The yield was 3 g, m.p. 88°–89° C.

SYNTHESIS EXAMPLE 2

Synthesis of leuco dye (7)

The compound (iv) was synthesized in the same manner as in Synthesis Example 1. In a flask were placed 10 g of the compound (iv) obtained above and 50 ml of acetonitrile. To the mixture were added 3.5 ml of benzoylchloride and 5 ml of pyrridine in order. The mixture was then stirred at room temperature for 2 hours. The reaction mixture was poured into a mixture of water and hydrochloric acid to obtain a crystalline precipitate. The precipitate was filtered to obtain a compound. The yield was 10.5 g, m.p. 170°–172° C.

In a flask were placed 5 g of the compound obtained above, 20 ml of ethyl acetate and 15 g of manganese dioxide, and the mixture was heated while stirring for 1 hour. The reacted mixture was filtered and concentrated under reduced pressure, and then recrystallized from acetonitrile to obtain a leuco dye (7). The yield was 4.25 g, m.p. 129°–130° C.

SYNTHESIS EXAMPLE 3

Synthesis of leuco dye (12)

A leuco dye (12) was prepared by the procedures similar to those of Synthesis Example 2 (m. p. 129°–130° C.).

The other leuco dyes can be also prepared by procedures similar to those of Synthesis Examples 1, 2 and 3.

In the recording material of the invention, the leuco dye having the formula (I) is preferably contained in an amount of 0.05 to 10 g/m$^2$, more preferably in an amount of 0.1 to 2 g/m$^2$.

The leuco dye having the formula (I) may be used singly or in combination. Other leuco dyes can be used in combination with the leuco dye of the invention to obtain various kinds of color images. The other leuco dye may have the same hue as that of the leuco dye of the invention or not. Examples of other leuco dyes include a triarylmethane compound, a diphenylmethane compound, a xanthene compound, a thiazine compound, a spiro-compound and mixtures of these compounds.

The leuco dye contained in the recording material of the invention develops a color on contact with an acid color developer. In the case that the acid color developer is also contained in the recording material of the invention, the developer is arranged out of contact with the leuco dye. For instance, the leuco dye is contained in microcapsules and the acid color developer is arranged outside of the microcapsules in the recording material. Alternatively, the leuco dye and the developer can be contained in separate layers respectively. In the image forming process, the recording material is pressed or heated so that the leuco dye comes into contact with the acid color developer. In another embodiment, the acid color developer can be contained in a material different from the recording material of the invention containing the leuco dye. In the image forming process, the recording material is pressed or heated on the material containing the developer so that the leuco dye comes into contact with the developer. In these embodiment, the acid color developer can be contained in microcapsules which are different from those containing the leuco dye.

In the case that the recording material of the invention is used as a pressure-sensitive material or a light-sensitive material, the leuco dye is preferably contained in microcapsules. More preferably, the acid color developer is contained in another layer which is different from the layer of the microcapsules. The layer containing the developer can be provided on a material (a developer sheet or an image-receiving material) different from the recording material of the invention. In the case that the microcapsules are employed as mentioned above, the obtained color image can be improved in the sensitivity and sharpness.

In the image forming process, the leuco dye preferably comes into contact with the acid color developer at an elevated temperature. The color forming reaction can be greatly accelerated by heating the leuco dye and the developer. Heating temperature for the reaction usually ranges from 50° C. to 200° C., and preferably from 50° C. to 150° C. The heating time is usually from 1 second to 1 minute, and preferably from 1 second to 10 seconds.

Examples of the acid color developers include an acid clay developer (e.g., China clay), phenol-formaldehyde resins (e.g., p-phenylphenol-formaldehyde resin), metal salts of salicylic acids (e.g., zinc 3,5-di-α-methylbenzyl salicylate), phenol-salicylic acid-formaldehyde resin (e.g., p-octylphenol-zinc salicylate-formaldehyde resin), zinc rhodanide and zinc xanthate.

Among them, the metal salts of the salicylic acids are preferred, and zinc salicylates are most preferred. It has been found that the reaction of the color formation of the leuco compound proceeds rapidly and effectively in the presence of zinc salicylates. The metal salts of the salicylates are described in more detail in Japanese Patent Publication No. 52(1977)-1327. The oilsoluble color developers containing zinc salicylates are described in U.S. Pat. Nos. 3,864,146 and 4,046,941.

The acid color developer is preferably used in an amount of from 50 to 1,000 weight % based on the amount of the leuco dye, and more preferably from 100 to 1,000 weight %.

The leuco dye of the present invention can be used in any pressure-sensitive, heat-sensitive and light-sensitive materials. However, the developed yellow color of the leuco dye is especially suitable for a monochromatic recording material. Therefore, the recording material of the invention is preferably used as a pressure-sensitive material or a heat-sensitive material.

The pressure-sensitive material of the invention is described in more detail hereinbelow.

The pressure-sensitive material generally comprises a layer (or sheet) containing the leuco dye and a layer (or sheet) containing the acid color developer. The sheet comprises a layer containing the leuco dye or the acid color developer provided on a support.

The layer containing the leuco dye preferably contains a binder. The leuco dye is preferably contained in microcapsules which are dispersed in the layer.

The microcapsules containing the leuco dye can be prepared in the following manner.

The leuco dye is dissolved or dispersed in an appropriate organic solvent and the resulting solution or dispersion (oil liquid) is emulsified in an aqueous medium.

The organic solvent preferably has a boiling point of not lower than 180° C., because a low-boiling organic silvent suffers an evaporation loss during storage. Examples of the organic solvents include an phosphoric ester, a phthalic ester, a carboxylic acid ester, a fatty acid amide, an alkylated biphenyl, an alkylated terphenyl, a chlorinated paraffin, an alkylated naphthalene and a diarylethanol.

Concrete examples of the organic solvents include tricresyl phosphate, trioctyl phosphate, octyl diphenyl phosphate, tricyclohexyl phosphate, dibutyl phthalate, dioctyl phthalate, dilauryl phthalate, dicyclohexyl phthalate, butyl oleate, diethylene glycol dibenzoate, dioctyl sebacate, dibutyl sebacate, dioctyl adipate, trioctyl trimellitate, acetyltriethyl citrate, octyl maleate, dibutyl maleate, isopropylbiphenyl, isoamylbiphenyl, chlorinated paraffin, diisopropylnaphthalene, 1,1'-ditolylethane, 2,4-di-tert-amylphenol and N,N-dibutyl-2-butoxy-5-tert-oxtylaniline. A vinyl compound can also be used as the organic solvent.

The leuco dye of the invention is preferably used in an amount of from 2 to 20 weight % based on the amount of the organic solvent.

The oil droplets in the emulsion is then processed for forming shell of the microcapsules.

There is no specific limitation on shell material of the microcapsule, and various known materials such as polymers can be employed as the shell material. Examples of the shell material include polyurethane, polyurea, polyamide, polyester, urea/formaldehyde resin, melamin resin, polystyrene, styrene/methacrylate copolymer, styrene/acrylate copolymer and mixtures thereof.

The microcapsule can be prepared by any of conventional methods without specific limitations. However an interfacial polymerization method and an internal polymerization method are preferred in the invention.

When polyurea and/or polyurethane is used as the shell material of the microcapsule, a polyisocyanate is mixed with a second material capable of reacting with the polyisocyanate to form the shell (e.g., polyol or polyamine) in an aqueous medium or an oil liquid to be encapsulated and the mixture is emulsified and dispersed in water and then heated. Thus, a polymerization reaction takes place at the interface of oil droplets to form the shell of the microcapsule.

In the process for formation of the microcapsule, a water-soluble polymer can be used as a protective colloid. The water-soluble polymer is preferably anionic, nonionic or amphoteric.

The anionic polymer used as the protective colloid may be either a natural substance or a synthetic substance. The anionic polymer preferably has carboxyl group or sulfo group. Examples of the anionic polymers include natural substances such as gum arabic and alginic acid; semisynthetic substances such as carboxymethylcellulose, phthalated gelatin, sulfated starch, cellulose sulfate and lignin sulfonic acid; and synthetic substances such as a maleic anhydride copolymer and hydrolyis products thereof, a (meth)acrylic acid polymer and copolymers thereof, a vinylbenzene-sulfonic acid polymer and copolymers thereof and a carboxy-modified polyvinyl alcohol. Examples of the nonionic polymers include polyvinyl alcohol, hydroxyethylcellulose and methylcellulose. An example of the amphoteric polymer is gelatin.

These water-soluble polymers (protective colloids) are preferably used in the form of an aqueous solution. The polymer is preferably contained in the solution in an amount of 0.01 to 10 weight %.

Examples of the binder which can be used in the layer containing the leuco dye include polyvinyl alcohol, methylcellulose, carboxymethylcellulose, hydroxypropylcellulose, gum arabic, gelatin, polyvinyl pyrrolidone, casein, styrene/butadiene latex, acrylonitrile/butadiene latex, polyvinyl acetate, polyacrylic ester and ethylene/vinyl acetate copolymer. These binders are preferably used in the form of an emulsion.

The binder is used in an amount of 0.5 to 5 g/m² on a solid basis.

The layer containing the leuco dye can be formed in such a manner that a microcapsule dispersion is mixed with a binder solution to prepare a coating solution and the coating solution is coated on a support according to a conventional coating method, such as bar coating, blade coating, air-knife coating, gravure coating, roll coating, spray coating and dip coating methods, and then dried.

The layer containing the leuco dye is usually provided in a range of 2.5 to 25 g/m² on a solid basis.

A paper support is preferably employed in the pressure sensitive material. A neutral paper having a pH of 6 to 9, which is measured according to a hot water extracting method, is preferably used as the paper support from the viewpoint of the storage stability of the recording material. The neutral paper support can be prepered, for instance, using a neutral size such as an alkylketene dimer. The surface of the paper support may be treated. The neutral paper support is described in more detail in Japanese Patent Provisional Publication No. 55(1980)-14281.

The layer (or sheet) containing the acid color developer can be formed in such a manner that an emulsion of the acid color developer is mixed with a binder to prepare a coating solution and the coating solution is coated on a support in a similar manner to that described above and then dried. The binder may be the same as that of the layer containing the leuco dye. The sheet containing the developer can be prepared using a different support from that of the pressure sensitive material.

The pressure-sensitive material containing a leuco dye is usually laminated on the sheet containing an acid color developer prior to use.

There are various embodiments other than that mentioned above. For instance, the leuco dye can be contained in different microcapsules from those containing the acid color developer and the two kinds of the microcapsules can be contained in the same layer (or sheet layer). In other embodiment, the leuco dye can be contained in a different layer from that containing the acid color developer and both layers are provided on the same support. In this embodiment, the pressure-sensitive material has a multilayer structure.

In the recording process employing the pressure-sensitive material of the present invention, external pressure, for instance handwriting or typewriting pressure breaks the microcapsules and releases the leuco dye, which reacts with the acid color developer to produce visible color.

The heat-sensitive material (thermal recording material) of the invention is described in more detail hereinbelow.

The heat-sensitive material has basically the same structure as that of the aforementioned pressure-sensitive material. The heat-sensitive recording material comprises a heat-sensitive layer (thermal recording layer) provided on a support. The leuco dye of the invention contained in the heat-sensitive layer. The acid color developer is preferably contained in the same layer as that of the leuco dye in consideration of saving thermal energy required for thermal response and color formation. The leuco dye is preferably contained in microcapsules which are dispersed in the heat-sensitive layer.

The shell material of the microcapsule preferably is a polymer which is impermeable at room temperature and becomes permeable at an elevated temperature. The polymer more preferably has a glass transition temperature of from 60° to 200° C. The shell material most preferably is polyurea or polyurethane.

The thermal recording process employing the heat-sensitive material of the invention is carried out, for instance, in the following manner.

The heat-sensitive material is arranged such that it is in contact with a heating element (printing head) such as thermal needle or thermal head. The heating element is heated in series corresponding to electric signals having image information transmitted from facsimile or electronic computer, and it scans the heat-sensitive material in a direction at the same time while it is in contact with the material. When the heat-sensitive material is moved in a direction perpendicular to the scanning direction of the heating element, a two-dimensional printing or image can be formed on the heat-sensitive material.

While the typical recording materials of the invention have been described above, the recording material of the invention can be used as other recording materials such as a light-sensitive material, an electrothermal recording sheet, an ultrasonic recording sheet, an electron beam recording material and an electrostatic recording material.

Examples of the light-sensitive materials include a recording sheet comprising a photosensitive resin (e.g., photoresist material) and a light-sensitive material comprising a light-sensitive layer containing silver halide, a reducing agent and a polymerizable compound provided on a support, which is described in Japanese Patent Provisional Publication No. 61(1986)-69026 (corresponding to U.S. Pat. No. 4,629,676) as well as a conventional silver salt photo-sensitive material. In the light-sensitive material containing silver halide, a reducing agent and a polymerizable compound, the leuco dye and the polymerizable compound are preferably contained microcapsules which are dispersed in the light-sensitive layer, while the acid color developer is preferably contained in an image-receiving material. The light-sensitive material is pressed on the image-receiving material after image exposure and development. The present invention is further described by the following examples without limiting the invention thereto. In the following examples, "part(s)" means "weight part(s)", unless otherwise indicated.

EXAMPLE 1

Preparation of pressure-sensitive material

In 95 parts of hot water at about 80° C. was dissolved 5 parts of partial sodium salt of polyvinylbenzenesulfonic acid (VERSA, TL500, average molecular weight; 500,000; produced by National Starch Co.) while stirring over 30 minutes. The aqueous solution was then cooled. The resulting aqueous solution having a pH of from 2 to 3 was adjusted to pH of 4.0 using 20 weight % aqueous solution of sodium hydroxide.

In 100 parts of the obtained 5% aqueous solution of partial sodium salt of polyvinylbenzenesulfonic acid was emulsified 100 parts of 3.5 weight % diisopropylnaphthalene solution of the following leuco dye (1) to obtain an emulsion of oily droplets having average droplet size of 4.5 μm.

(Leuco dye (1))

-continued

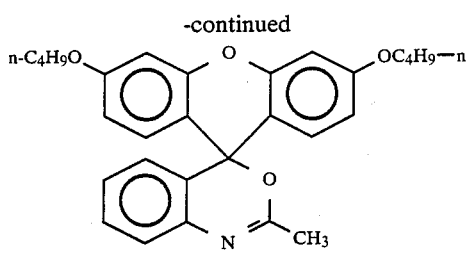

Separately, 6 parts of melamine, 11 parts of 37 weight % aqueous solution of formaldehyde and 30 parts of water were heated to 60° C. while stirring. After 30 minutes, a clear aqueous solution of a mixture (precondensate) of melamine, formaldehyde and a malamineformaldehyde precondensate was obtained. The aqueous solution had a pH of 6 to 8.

To the emulsion was added the precondensate solution obtained above. The resulting mixture was adjusted to pH of 6.0 using 3.6 weight % aqueous solution of phosphoric acid while stirring. The mixture was then heated to 65° C. while stirring for 6 hours to obtain a microcapsule dispersion. The dispersion was then cooled to room temperature and adjusted to pH of 9.0 using 20 weight % aqueous solution of sodium hydroxide.

To the microcapsule dispersion were added 200 parts of 10 weight % aqueous solution of polyvinyl alcohol (PVA-117, produced by Kuraray Co., Ltd.) and 50 parts of starch particles. To the mixture was further added water to obtain a coating solution having solid content of 20%. The coating solution was coated on the surface of a base paper having basis weight of 50 g/m² in coating amount of 5 g/m² based on the solid content using an air-knife coater and then dried to obtain a pressuresensitive material (I).

EXAMPLES 2 AND 3

Pressure-sensitive materials (II) and (III) were prepared in the same manner as in Example 1, except that the following leuco dyes (7) and (12) were respectively used in place of the leuco dye (1).

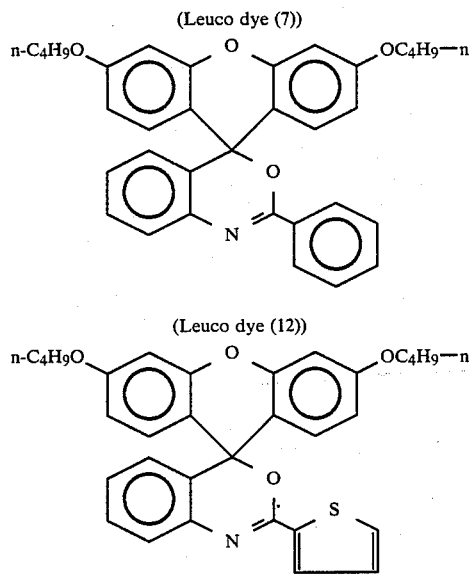

COMPARISON EXAMPLES 1 AND 2

Pressure-sensitive materials (IV) and (V) were prepared in the same manner as in Example 1, except that the following conventional leuco dyes (a) and (b) were respectively used in place of the leuco dye (1).

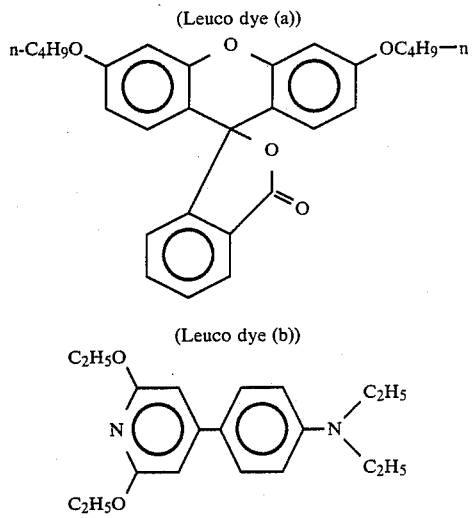

Preparation of sheet containing acid color developer

To 20 parts of 1-isopropylphenyl-2-phenylethane was added 10 parts of zinc 3,5-bis-α-methylbenzylsalicylate, and the mixture was heated at 90° C. to obtain a solution. The solution was added to 50 parts of 2 weight % aqueous solution of polyvinyl alcohol (PVA-117; produced by Kuraray Co., Ltd.), and 0.1 part of 10% aqueous solution of triethanolamine dodecylbenzenesulfonate (surfactant) was further added to the mixture. The resulting mixture was stirred using a homogenizer to obtain an emulsion having average droplet size of 3 μm.

A dispersion containing 80 parts of calcium carbonate and 20 parts of zinc oxide was prepared using a mill, and the dispersion was mixed with the emulsion. To the mixture were further added 100 parts of 10 weight % aqueous solution of polyvinyl alcohol (PVA-117; produced by Kuraray Co., Ltd.) as binder and 10 parts of a carboxy-modified SBR latex (SN-307; produced by Sumitomo Naugatax Co.) as solid content. To the mixture was then added water to obtain a coating solution (A) having solid content of 20%.

Separately, a mixture containing 15 parts of zinc 3,5-bis-α-methyl-benzylsalicylate, 20 parts of silty clay (Silton Clay, tradename of Mizusawa Chemical Co., Ltd.), 60 parts of calcium carbonate, 20 parts of zinc oxide, 1 part of sodium hexametaphosphate and 200 parts of water was stirred using a sand grinder to obtain a dispersion having average particle size of 3 μm.

To the resulting dispersion was added 16 parts of a 10 weight % aqueous solution of polyvinyl alcohol (PVA-103; produced by Kuraray Co., Ltd.). To the mixture were added 100 parts of 10 weight % aqueous solution of polyvinyl alcohol (PVA-117; produced by Kuraray Co., Ltd.) and 10 parts of carboxy-modified SBR latex (SN-307; produced by Sumitomo Naugatax Co.) as solid content. To the mixture was then added water to obtain a coating solution (B) having solid content of 20%.

The coating solution (A) was mixed with the coating solution (B) in the ratio of 50 (A) to 50 (B) in terms of the amount of acid color developer. The mixture was coated on the surface of a base paper having basis weight of 50 g/m² in coating amount of 5.0 g/m² based on the solid content using an air-knife coater and then dried to obtain a sheet containing acid color developer.

Evaluation of pressure-sensitive material

Each of the pressure-sensitive materials (I) to (V) was pressed on the sheet containing an acid color developer and the density of each of the yellow images obtained on the sheet was measured using a reflection densitometer.

Further, the light fastness of the obtained image was evaluated according to the following manner.

Each of the yellow images was irradiated with light using xenon lamp at 80,000 lux for 3 hours. And then, the discoloration was evaluated measuring the density of the remaining color image and comparing the density with that before the irradiation.

The results are set forth in Table 1. In Table 1, "Remaining Ratio after Irradiation" means the ratio of the density of the color image after the irradiation to that before the irradiation.

TABLE 1

| Pressure-sensitive Material | Leuco Dye | Color Density | Remaining Ratio after Irradiation |
|---|---|---|---|
| (I) | (1) | 1.03 | 96% |
| (II) | (7) | 1.02 | 93% |
| (III) | (12) | 1.05 | 95% |
| (IV) | (a) | 0.72 | 82% |
| (V) | (b) | 0.52 | 65% |

It is apparent from the results in Table 1 that each of the pressure-sensitive materials of the present invention (I) to (III) forms an improved color image which has a high maximum density and the light fastness of the image is also improved, compared with the pressure-sensitive materials (IV) and (V) containing a conventional leuco dye. Further, it is observed that the color developing rate is also improved in the pressure-sensitive materials (I) to (III).

We claim:

1. A recording material comprising a support and a layer containing a leuco dye, wherein the leuco dye has the formula (I):

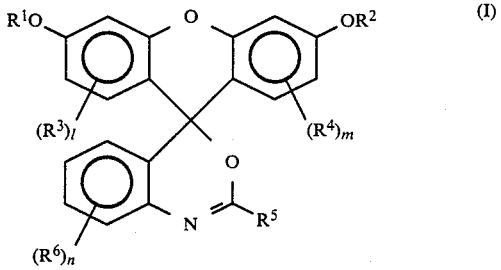

in which each of $R^1$ and $R^2$ independently is a monovalent group selected from the group consisting of an alkyl group, a cycloalkyl group and an aralkyl group; each of $R^3$ and $R^4$ independently is a monovalent group selected from the group consisting of a halogen atom, an alkyl group, a cycloalkyl group, and aralkyl group, an alkoxy group and an acylamino group; $R^5$ is a monovalent group selected from the group consisting of an alkyl group, a cycloalkyl group, and aralkyl group, an alkoxy group, an aryloxy group, a dialkylamino group, an alkoxycarbonyl group, an aryloxycarbonyl group, a dialkylcarbamoyl group, an aryl group and a heterocyclic group; $R^6$ is a monovalent group selected from the group consisting of a halogen atom, an alkyl group, an alkoxy group, hydroxyl, amino, an alkylamino group, an dialkylamino group, an acylamino group, nitro, cyano, carbamoyl, sulfamoyl, an arloxycarbonyl group, an alkoxycarbonyl group, an alkylsulfonyl group, an arylsulfonyl group, an alkylsulfonylamino group, an arylsulfonylamino group and an aryl group; l is 0 or 1; m is 0 or 1; n is 0, 1, 2, 3 or 4 (when n is 2, 3 or 4, the groups represented by $R^6$ may be different from each other); each of $R^1$, $R^2$, $R^3$, $R^4$, $R^5$ and $R^6$ may have one or more substituent groups.

2. The recording material as claimed in claim 1, wherein each of $R^1$ and $R^2$ independently is an alkyl group or an aralkyl group.

3. The recording material as claimed in claim 1, wherein each of $R^1$ and $R^2$ independently is an alkyl group.

4. The recording material as claimed in claim 1, wherein each of $R^3$ and $R^4$ independently is a monovalent group selected from the group consisting of a halogen atom, an alkyl group and a cycloalkyl group.

5. The recording material as claimed in claim 1, wherein $R^5$ is a monovalent group selected from the group consisting of an alkyl group, a cycloalkyl group, an alkoxy group, and alkoxycarbonyl group, an aryl group and a heterocyclic group.

6. The recording material as claimed in claim 1, wherein $R^5$ is a monovalent group selected from the group consisting of an alkyl group, and aryl group and a heterocyclic group.

7. The recording material as claimed in claim 1, wherein $R^6$ is a monovalent group selected from the group consisting of a halogen atom, an acylamino group and an alkylsulfonyl group.

8. The recording material as claimed in claim 1, wherein n is 0.

9. The recording material as claimed in claim 1, wherein the recording material is a pressure-sensitive recording material or a heat-sensitive recording material.

10. The recording material as claimed in claim 1, wherein the leuco dye is contained in microcapsules which are dispersed in the layer provided on the support.

11. The recording material as claimed in claim 1, wherein the leuco dye is contained in the layer in an amount of 0.05 to 10 g/m².

12. The recording material as claimed in claim 1, wherein the layer containing the leuco dye further contains an organic solvent, the amount of said leuco dye ranging from 2 to 20 weight % based on the amount of the organic solvent.

* * * * *